(12) United States Patent
Sundheimer et al.

(10) Patent No.: US 9,237,883 B2
(45) Date of Patent: Jan. 19, 2016

(54) FULL CORE BIOPSY DEVICE

(75) Inventors: Herbert Alan Sundheimer, Franklin, IN (US); Dan C. Ireland, Martinsville, IN (US)

(73) Assignee: JJ Dogs LLC, Indianapolis, IN (US)

( * ) Notice: Subject to any disclaimer, the term of this patent is extended or adjusted under 35 U.S.C. 154(b) by 1019 days.

(21) Appl. No.: 12/970,761

(22) Filed: Dec. 16, 2010

(65) Prior Publication Data

US 2011/0208089 A1     Aug. 25, 2011

Related U.S. Application Data

(60) Provisional application No. 61/368,119, filed on Jul. 27, 2010, provisional application No. 61/308,024, filed on Feb. 25, 2010.

(51) Int. Cl.
*A61B 10/00* (2006.01)
*A61B 10/02* (2006.01)
*A61B 17/3205* (2006.01)
*A61B 17/32* (2006.01)

(52) U.S. Cl.
CPC ......... *A61B 10/0233* (2013.01); *A61B 10/0266* (2013.01); *A61B 10/0283* (2013.01); *A61B 17/32053* (2013.01); *A61B 2010/0093* (2013.01); *A61B 2017/320064* (2013.01)

(58) Field of Classification Search
CPC ........... A61B 10/0266; A61B 10/0233; A61B 17/32053; A61B 2017/320064
USPC ......... 600/567, 573, 564, 431, 458, 179, 566; 606/159, 170
See application file for complete search history.

(56) References Cited

U.S. PATENT DOCUMENTS

| | | | |
|---|---|---|---|
| 4,512,344 A | | 4/1985 | Barber |
| 4,907,598 A | | 3/1990 | Bauer |
| 5,313,958 A | | 5/1994 | Bauer |
| 5,400,798 A | | 3/1995 | Baran |
| 5,490,521 A | * | 2/1996 | Davis et al. ............ 600/458 |
| 5,535,755 A | | 7/1996 | Heske |
| 5,615,690 A | * | 4/1997 | Giurtino et al. ............ 600/567 |
| 5,655,542 A | * | 8/1997 | Weilandt ............ 600/567 |
| 5,788,651 A | | 8/1998 | Weilandt |

(Continued)

FOREIGN PATENT DOCUMENTS

| | | |
|---|---|---|
| JP | SHO64-6915 | 1/1987 |
| JP | HEI8-140980 | 6/1996 |

(Continued)

OTHER PUBLICATIONS

Sales Sheet BioPrince Full-Core Biopsy Instruments, Angiotech PBN Medicals Denmark A/S Knud Bro Alle 3 KD-3660 Stenlose, date unknown.

(Continued)

*Primary Examiner* — Devin Henson
(74) *Attorney, Agent, or Firm* — Maginot, Moore & Beck, LLP (57) ABSTRACT

A biopsy device includes coaxially disposed inner and outer needles in which the outer needle tip is configured for obtaining a tissue sample. The inner surface of the outer needle includes a tissue retention feature which may include a countersink and/or a feature formed in the inner surface. The device may be configured such that the inner needle does not extend past a certain point within the outer needle.

13 Claims, 6 Drawing Sheets

(56) References Cited

U.S. PATENT DOCUMENTS

| | | | |
|---|---|---|---|
| 5,916,175 | A | 6/1999 | Bauer |
| 6,015,391 | A | 1/2000 | Rishton et al. |
| 6,083,237 | A | 7/2000 | Huitema et al. |
| 6,126,617 | A | 10/2000 | Weilandt et al. |
| 6,196,978 | B1 | 3/2001 | Weilandt et al. |
| 6,258,045 | B1 * | 7/2001 | Ray et al. ............ 600/573 |
| 6,322,523 | B2 | 11/2001 | Weilandt et al. |
| 6,416,484 | B1 * | 7/2002 | Miller et al. ............ 600/564 |
| 6,689,072 | B2 | 2/2004 | Kaplan et al. |
| 6,918,881 | B2 * | 7/2005 | Miller et al. ............ 600/567 |
| 7,137,956 | B2 | 11/2006 | Nishtalas et al. |
| 7,608,049 | B2 | 10/2009 | Goldenberg |
| 7,611,473 | B2 * | 11/2009 | Boock et al. ............ 600/564 |
| 8,157,746 | B2 * | 4/2012 | Eberle et al. ............ 600/564 |
| 2004/0167428 | A1 * | 8/2004 | Quick et al. ............ 600/564 |
| 2006/0217635 | A1 * | 9/2006 | McCombs et al. ............ 600/566 |
| 2007/0106176 | A1 | 5/2007 | Mark et al. |
| 2007/0142744 | A1 * | 6/2007 | Provencher ............ 600/562 |
| 2007/0156164 | A1 * | 7/2007 | Cole ............ A61B 17/32053 606/187 |
| 2008/0234602 | A1 * | 9/2008 | Oostman et al. ............ 600/564 |
| 2009/0143808 | A1 * | 6/2009 | Houser ............ 606/170 |
| 2009/0204020 | A1 | 8/2009 | Miller et al. |
| 2009/0275858 | A1 | 11/2009 | Hardin |
| 2011/0152715 | A1 | 6/2011 | Delap et al. |
| 2011/0208089 | A1 | 8/2011 | Sundheimer et al. |

FOREIGN PATENT DOCUMENTS

| | | |
|---|---|---|
| JP | 2008528217 | 7/2008 |
| RU | 13534 U1 | 4/2000 |
| SU | 1404068 A1 | 6/1988 |

OTHER PUBLICATIONS

BioPince product information, web page screen print Nov. 16, 2010, Angiotech Pharmaceutical, Inc., copyright datee 2007-2010.

W F Dahnert, et al., Fine-needle aspiration biopsy of abdominal lesions: diagnostic yield for different needle tip configurations, Radiology, Oct. 1992, abstract, vol. 185—iss.1, Radiological Society of North America, Inc.

* cited by examiner

FULL CORE BIOPSY DEVICE

CLAIM OF PRIORITY

This application claims priority to U.S. Provisional Application No. 61/368,119, entitled "Full Core Biopsy Device", which was filed on Jul. 27, 2010, the disclosure of which is incorporated herein by reference, and further claims priority to U.S. Provisional Application No. 61/308,024, entitled "Full Core Biopsy Device", which was filed on Feb. 25, 2010, the disclosure of which also is incorporated herein by reference.

BACKGROUND

The present invention relates to devices for obtaining a tissue biopsy sample, and more particularly to a device for obtaining a soft tissue core biopsy sample.

Clinicians obtain biopsy specimens for the purpose of diagnosing, staging and grading disease states. One type of biopsy device is a core biopsy needle, which typically operates by coaxial action of an inner needle or stylet having a specimen notch and an outer needle or cannula having a sharp end, with the tip of the inner stylet proud of the end of the outer cannula. The stylet is advanced so that the specimen notch is exposed to tissue, which prolapses into the notch. The cannula is then advanced over the stylet so that the sharp end of the cannula severs the tissue leaving the specimen in trapped within the notch. The volume of the specimen is limited by the notch and the inner diameter of the cannula.

In many biopsy situations, clinicians may desire a full, rounded core sample. The larger cross-section and volume of tissue can provide a more accurate assessment of the tissue pathology. It is also desirable to obtain full, clean core samples that have not been crushed by devices penetrating into tissue, since "crush artifacts" can compromise the analysis of the retrieved sample. In addition, the larger volume of the full core may often provide enough tissue so that only a single pass of the biopsy needle is required. Moreover, it may be desirable to obtain a core sample without having to penetrate past a desired depth of tissue in order to obtain a corresponding desired depth of core sample. It is preferable to insert a biopsy needle only as far as necessary to obtain the desired core sample.

There is a continuing need for biopsy devices, and particularly full core biopsy devices, which can quickly and efficiently obtain large, intact tissue samples. The need is particularly acute for soft tissue samples because the soft tissue can be difficult to extract and retain without damage to the tissue.

SUMMARY

In one aspect, a biopsy device comprises coaxially disposed inner and outer needles in which the outer needle includes an outer needle having a tissue slicing feature configured for cutting tissue and an inner surface including a tissue retention feature defined therein. In one embodiment, the tissue retention feature may include a countersink formed at the tip. The countersink may be tapered from the tip toward the distal end of the outer needle. In another aspect, the tissue retention feature may include a groove defined in the inner surface.

In another aspect of the disclosed embodiments, a biopsy device comprises coaxially disposed outer and inner needles and a mechanism coupled to the needles for charging and firing the outer needle relative to the inner needle to capture a tissue sample within the outer needle. The inner needle and the outer needle are sized so that the inner needle tip is always proximal of a distalmost end of the outer needle tip when the outer needle is charged and fired. In certain embodiments, the outer needle includes a tissue slicing feature having a plurality of prongs and valleys therebetween, with the valleys defining a base diameter. In one feature, the inner needle and the outer needle are sized so that the inner needle tip is always positioned between the proximal end of the outer needle and the valleys of the tissue slicing feature at a distance approximately equal to the base diameter. In yet another aspect, the prongs of the tissue slicing feature have a height and the inner needle and the outer needle are sized so that the inner needle tip is always positioned at a distance from the valleys approximately equal to one quarter of the height.

The present disclosure further provides a biopsy device having coaxially disposed inner and outer needles and a vacuum generating component. The vacuum generating component includes a chamber in communication with the proximal end of the inner needle, a piston coupled to the proximal end of the inner needle and slidably disposed within the chamber, and a handle coupled to the proximal end of the inner needle configured to manually pull the inner needle and the piston therewith to draw a vacuum within the chamber.

A method of obtaining a tissue sample is using a biopsy device is provided that comprises introducing the biopsy device into a tissue site where a tissue sample is to be obtained, obtaining the tissue sample with the outer needle and selectively drawing a vacuum in the inner needle to retain the tissue sample within the outer needle as the device is extracted from the tissue site. In one aspect, the vacuum is drawn only as the biopsy device is extracted from the tissue site.

An outer needle is provided for use in a biopsy device having an inner needle to be slidably disposed within the outer needle and a charging and firing mechanism coupled to the inner and outer needles to advance the outer needle over the inner needle to obtain a tissue sample. In one aspect, the outer needle comprises a proximal end to be coupled to the charging and firing mechanism, an outer needle tip at an opposite distal end, an outer surface having a tissue slicing feature at the tip configured for cutting tissue, and an inner surface including a countersink formed at the tip. The outer needle may further include an additional tissue retention feature defined in the inner surface between the tissue slicing feature and the proximal end of the outer needle, such as a spiral groove defined in the inner surface.

The above described features and advantages, as well as others, will become more readily apparent to those of ordinary skill in the art by reference to the following detailed description and accompanying drawings. While it would be desirable to provide a biopsy device that includes one or more of these advantageous features, the teachings disclosed herein extend to those embodiments which fall within the scope of the appended claims, regardless of whether they accomplish one or more of the above-mentioned advantages.

DETAILED DESCRIPTION

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 1:
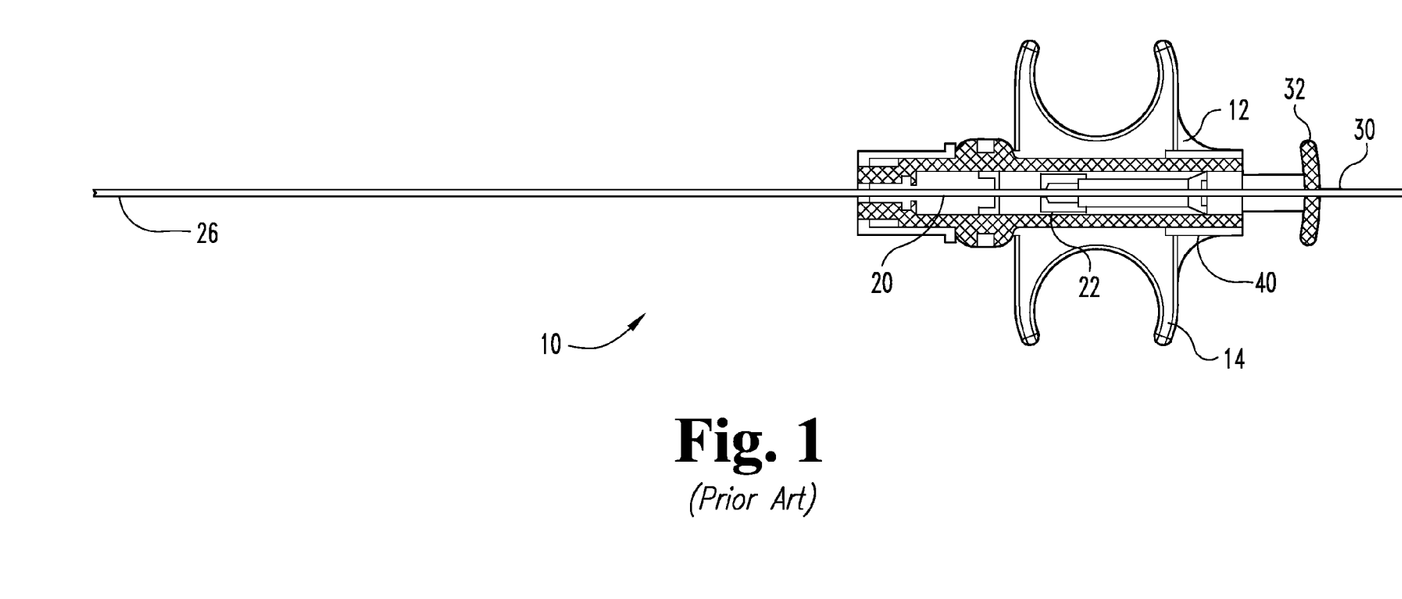
FIG. 1 is a top cross-sectional view of a full core biopsy device of the prior art.

One type of core biopsy device 10 is shown in FIG. 1. The device may include features found in the SABD™ core biopsy system sold by US Biopsy of Franklin, Ind., or similar devices capable of obtaining a core tissue sample from a patient. Although the present disclosure relates to a core biopsy device, the features disclosed herein may be incorporated into other types of tissue sampling or tissue biopsy devices. The device 10 includes a housing 12 that defines finger handles 14 to be grasped by the clinician during a biopsy procedure. The device can include an outer cannula or needle 20 and an inner stylet, cannula or needle 30 coaxially extending through the outer needle 20.

Figure 2:
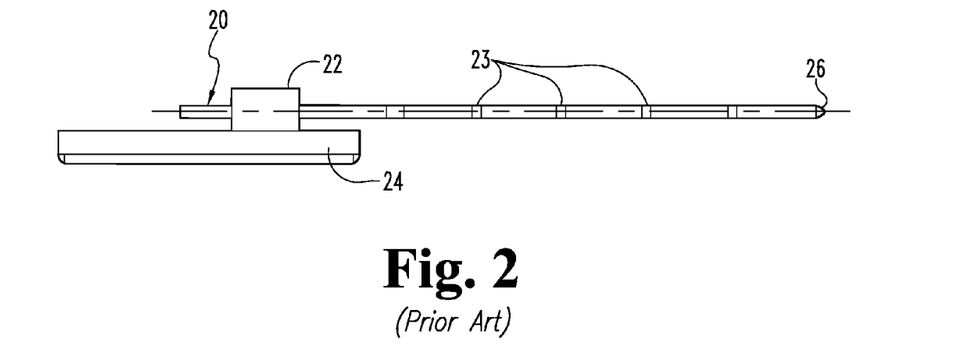
FIG. 2 is a side view of an outer needle component of the full core biopsy device shown in FIG. 1.
Figure 3:
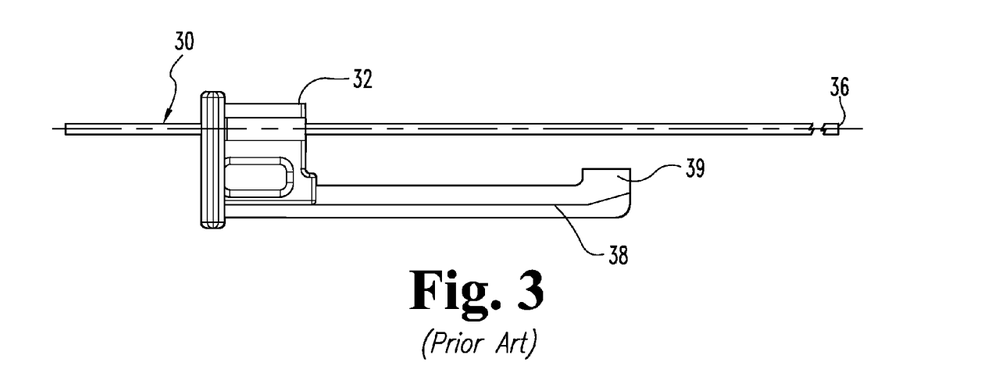
FIG. 3 is a side view of an inner needle component of the full core biopsy device shown in FIG. 1.

The biopsy device 10 incorporates a mechanism for charging and firing the outer needle relative to the inner needle in order to capture a tissue sample. One embodiment of a firing mechanism is described herein although other mechanisms are contemplated that permit charging and firing the outer needle relative to the inner needle to obtain a tissue sample, including semi or fully automated systems. As shown in more detail in FIG. 2, the outer needle 20 is fixed within an outer needle hub 22 mounted on an outer needle carriage 24. Similarly, as shown in FIG. 3, the inner needle 30 is fixed within an inner needle hub 32 mounted on an inner needle carriage 38. The inner needle carriage 38 includes a tab 39 for engaging the outer needle carriage 24 when the biopsy device 10 is charged. The outer needle 20 may include markings 23 used to determine the depth of the outer needle 20 upon insertion into the patient.

Referring back to FIG. 1, the device 10 includes a spring 40 disposed between the housing 12 and the outer needle hub 22. As is known, the device 10 may include a latch (not shown) that holds the outer needle 20 in its charged position. As with many similar biopsy devices, the device 10 is charged by pulling back on the inner needle hub 32, which in turn pulls the outer needle carriage 24 back until it is engaged by the latch. As the outer needle hub 22 is retracted it compresses the spring 40 within the housing 12.

The biopsy device 10 may be fired by pushing the inner needle hub 32 forward so that the tab 39 trips the latch, although other firing mechanisms may be implemented. Once the latch is released the spring 40 propels the outer needle 20 forward over the inner needle and into the subject tissue. In a biopsy procedure, the clinician positions the tip 26 of the outer needle 20 against the tissue to be sampled, with the device in its charged position. When the device is fired, the outer needle 20 advances directly into the tissue so that a core of tissue is captured within the lumen 21 (FIG. 5) of the outer needle 20. The device 10 can be removed from the patient and the tissue core retrieved from the outer needle 20 in a known manner.

As thus far described, the device 10 may be similar in structure and operation to the SABD™ biopsy system and other similar coaxial single action core biopsy devices. The present invention provides improvements to devices of this type and more particularly improvements to the outer and inner needles for use with such devices. However, it is understood that the features described herein may be incorporated into other types of tissue sampling or biopsy devices.

Figure 4:
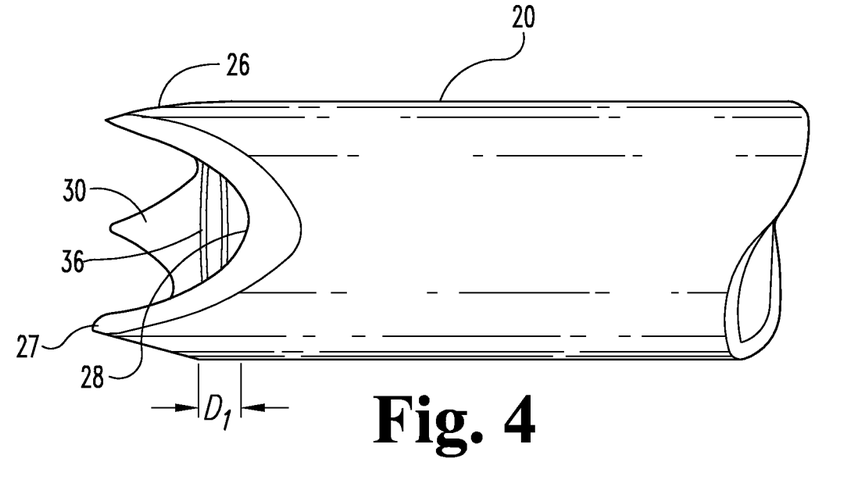
FIG. 4 is an enlarged side view of the end of an outer needle component for use with the full core biopsy device shown in FIG. 1, with the inner needle in its extended position.
Figure 5:
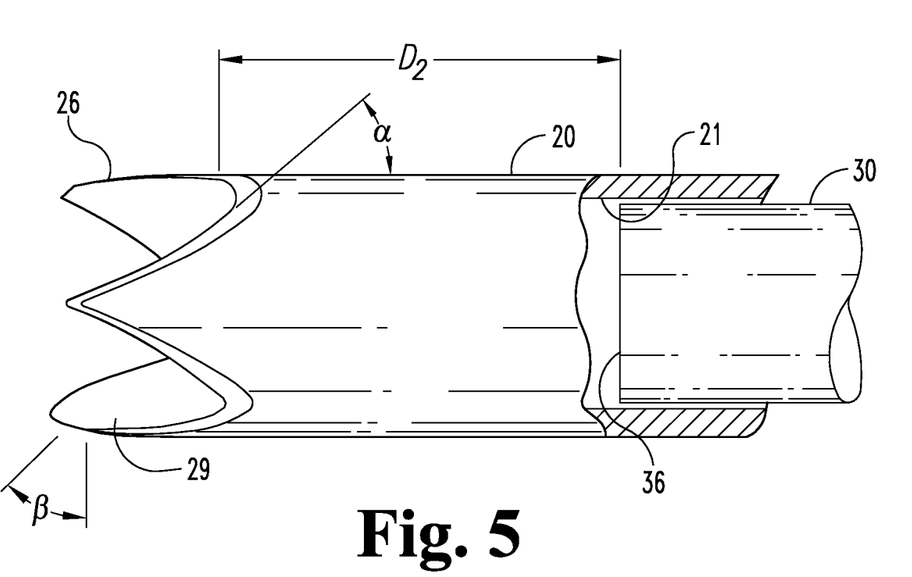
FIG. 5 is an enlarged side view of the end of the outer needle component for use with the full core biopsy device shown in FIG. 1, with the inner needle in its retracted position.

According to one aspect, the outer needle 20 is provided with a Franseen tip 26, as shown in FIGS. 4-5. The Franseen tip includes three or more prongs 27 separated by valleys 28 around the circumference of the outer needle tip 26. In one specific embodiment, three prongs 27 are each defined at an angle $\alpha$, which may be about 18°. The edge surfaces 29 of the prongs 27 may be defined at an angle $\beta$, which may be about 30°, to form a sharp cutting edge within the valleys 28. The prongs 27 permits smooth piercing of the soft tissue as the outer needle 20 initially advances into the tissue and solid purchase once the outer needle has been fully advanced. The prongs 27 are configured to advance through the tissue without substantially compressing the tissue. The angled edge surfaces 29 of the prongs 27 act as guillotine cutters to slice cleanly through the tissue as the outer needle 20 advances.

In accordance with one aspect of the disclosed embodiments, the inner needle 30 is maintained in a retracted position relative to the tip 26 of the outer needle 20 when the device 10 is charged as well as when the device 10 is fired. Thus, as shown in FIG. 4, the tip 36 of the inner needle 30 extends only a dimension D1 from the base of the valleys 28 of the tip 26 when the inner needle hub 32 has been moved to trip the latch and release the outer needle 20 as explained above. When the device 10 is initially charged the inner needle tip 36 preferably does not extend beyond, or extends only minimally beyond, the base of the valleys 28 of the tip 26 of the outer needle 20. Put another way, the tip 36 of the inner needle 30 is always offset rearward from the distalmost ends of the prongs 27 of the tip 26 of the outer needle 20, as depicted in FIG. 4. In one embodiment, the dimension D1 is less than about one-fourth of the length of the prongs 27 (i.e., the distance between the base of the valleys 28 and the distal end or top of the prongs 27).

It can be appreciated that in the charged position shown in FIG. 4, the inner needle hub 32 is in position to fire the device 10. Since the device 10 is fired by moving the inner needle hub 32 forward, as explained above, the tip 36 of the inner needle 30 may contact soft tissue if it resides too proud of the outer needle 20. In prior devices the inner stylet extends beyond the end of the outer cutting cannula prior to firing which tends to push the soft tissue away from the cutting cannula, resulting in less than a full core sample or a sample with a crush artifact. In the embodiments disclosed herein, the arrangement of the inner needle 30 relative to the outer needle 20 in the charged and firing positions avoids this condition found in prior devices. It can be appreciated that this positional relationship is produced by appropriate sizing of the length of the outer needle 20 and inner needle 30 taking into account the configuration of the charging and firing mechanism. The inner needle 30 thus has a length that maintains the inner needle tip 36 in the position shown in FIG. 4 when the inner needle hub 32 has been advanced to release the latch holding the outer needle hub 22 against the compressed firing spring 40.

In yet another approach, the inner needle 30 can be mounted within the inner needle hub 32 to permit deliberate retraction of the inner needle 30 prior to firing to ensure that the inner needle tip 36 is clear of the outer needle tip 26. Thus, a threaded arrangement may be incorporated between the inner needle 30 and the inner needle hub 32 configured so that rotation of the inner needle 30 backs the needle out from the inner needle hub 32. As the inner needle 30 backs out relative to the inner needle hub 32, the inner needle tip 36 is retracted from the outer needle tip 26. The threaded engagement may be configured to prevent complete disengagement of the inner needle 30 from the inner needle hub 32 and may preferably incorporate a locking mechanism to lock the inner needle 30 in its retracted position when the biopsy device 10 is fired. With this embodiment, once the biopsy device 10 is charged the clinician takes the additional step of rotating the inner needle 30 to retract the tip 36 prior to firing the device. The inner needle 30 may be provided with a finger tab at its proximal end to facilitate manual rotation of the needle.

As shown in FIG. 5, after the device 10 is fired, the inner needle 30 is offset rearward from the tip 26 of the outer needle 20 by a dimension D2 because the outer needle 20 has been driven forward by the firing spring 40. This dimension is calibrated to the length of the tissue core desired and is generally based on the throw of the device 10 achieved by the charging and firing mechanism—i.e., the distance that the outer needle 20 travels when propelled by the spring 40. In certain full core biopsy devices the throw of the outer needle may be fixed, while in other such devices the throw may be adjustable to vary the length of the tissue sample that is obtained.

After the device has been fired, the excised tissue sample is retained within the end of the outer needle 20. The inner needle 30 may then be used to expel the tissue sample. This can be accomplished by charging the device—i.e., by pulling back on the inner needle hub 32—which withdraws the outer needle 20 to its initial charged position. With the outer needle 20 charged, the inner needle 30 can be freely advanced forward far enough to push the tissue sample out of the outer needle 20, but not so far as to release the latch and dry fire the device 10. The inner needle 30 would thus be advanced to the position shown in FIG. 4. Since the inner needle 30 is used to expel the sample, it is desirable that the tip 36 of the inner needle 30 be immediately proximate the base of the valleys 28 of the tip 26 of the outer needle 20. This position of the inner needle tip 36 will ensure that the soft tissue sample is dislodged from the outer needle 20 either freely or with only minor urging so as not to destroy the sample.

In certain uses of the device 10 the preferred initial step may be to insert an introducer and stylet to the biopsy site. The stylet is removed and the device 10 is charged and passed through the introducer until the outer needle tip 26 is initially engaged with the soft tissue. The device 10 is then fired and removed through the introducer. To remove the biopsy sample, the device 10 is charged again and the inner needle 30 is slowly advanced forward as the device 10 itself is moved backward over the receiving surface (similar to putting icing on a cake). Once the inner needle 30 reaches the end of its stroke, the biopsy sample should be fully and cleanly dislodged from the outer needle 20.

It can be appreciated that the action of the inner needle 30 is an important factor in producing an intact full-core biopsy sample. The inner needle tip 36 may be closed so that tissue cannot migrate into the inner needle 30. The inner needle tip 36 may be slightly concave to urge the trailing tissue toward the center of the inner needle 30. The inner needle 30 is sized for a close running fit within the inner lumen 21 of the outer needle 20 (FIG. 5), and to prevent passage of tissue into the gap between the inner needle 30 and outer needle 20.

It can be appreciated that the combination of the Franseen tip 26 and the relative positioning between the inner needle 30 and outer needle 20 described above provides a significantly greater chance of obtaining a full, clean core biopsy sample that has not been crushed without having to penetrate past a desired depth of tissue in order to obtain a corresponding desired depth of core sample. The Franseen tip 26 of the device 10 provides a cleaner cut with only linear motion and without rotation of the outer needle 20. This helps reduce the chance of crushing the sample. The relative position of the inner needle 30 and the outer needle 20 also reduces the chance of crushing the sample and helps reduce the depth in the tissue that the device 10 must travel to obtain its full, clean core biopsy sample.

Figure 6:
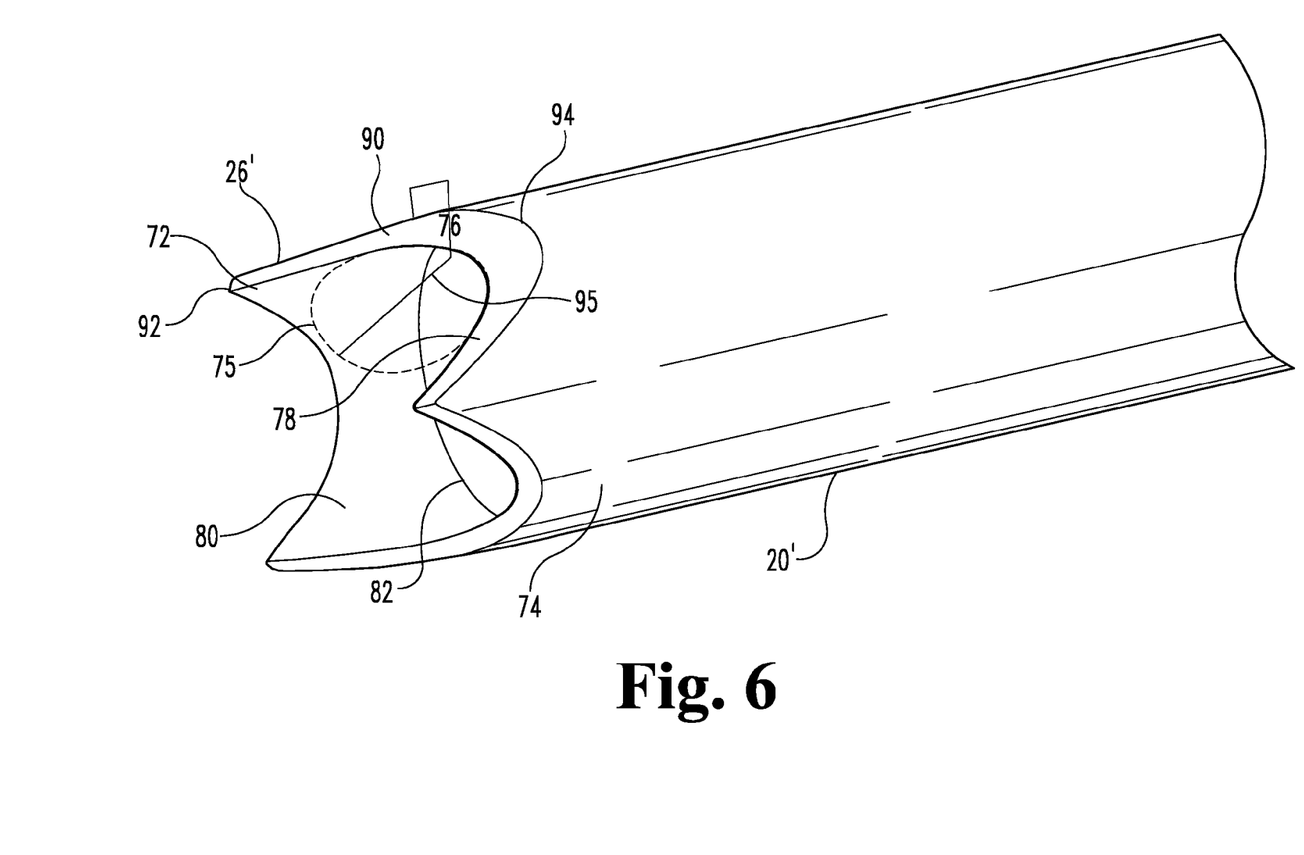
FIG. 6 is an enlarged view of an outer according to a further embodiment for use with the full core biopsy core device of FIG. 1.
Figure 7:
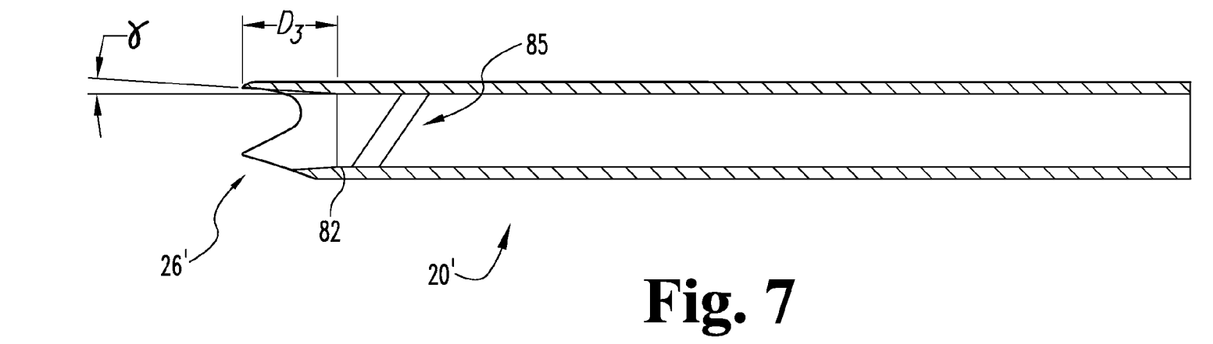
FIG. 7 is a side cross-sectional view of the outer needle component shown in FIG. 6.

In another embodiment, shown in FIGS. 6-7, an outer needle 20' includes an inner surface 72 and an outer surface 74. The outer needle 20' defines a thickness 76 between the inner surface 72 and the outer surface 74. In one aspect, the inner surface of the outer needle includes features for enhancing retention of the tissue within the outer needle once the device has been fired. Thus, in one embodiment, this retention feature includes a countersink or forcing cone 80 defined in the inner surface 72. The forcing cone further leads to a sharper cutting edge 78 at the tip of the outer needle.

The countersink or forcing cone 80 is formed in the inner surface 72 of the outer needle 20' and extends from the tip to an inner end 82. The inner end 82 is located at a depth D3 that may be, in certain embodiments, approximately twice the diameter 95 defined by the valley 75 between the prongs 92 the tip 26'. The forcing cone 80 is formed such that the thickness 76 of the outer needle 20' is greater at the inner end 82 than at the tip 26'. In other words, the thickness at the inner end 82 is equal to the wall thickness of the tubular body of the outer needle 20' but tapers to a sharp cutting edge 78 at the tip 26'. The forcing cone 80 is formed in the inner surface 72 at an angle γ as shown in FIG. 7. In certain embodiments, the angle γ may be about 3-4° so that the countersink or forcing cone 80 forms an included angle of about 6-8°.

The forcing cone 80 assists in retaining the tissue within the outer needle when the device is fired and when the excised tissue is being removed. It is believed that the forcing cone tends to compress a greater volume of tissue into the outer cannula during the coring operation and that this greater volume in turn provides additional surface tension or pressure between the tissue sample and the forcing cone 80. This increased pressure allows the tissue sample to "grip" the inner surface of the outer needle as the device is being extracted from the tissue site.

The cutting edge 78 is formed by the intersection of the forcing cone 80 with the outer surface 74. Because the countersink or forcing cone 80 decreases the thickness 76 of the outer needle 20', it produces a much sharper cutting edge 78. The thickness of the cutting edge 78 may be approximately 0.0005 to 0.001 inches.

In another aspect, the outer needle 20' may further include a tissue slicing feature 90 formed in the outer surface 74. The tissue slicing feature 90 also reduces the thickness 76 of the outer needle 20' so that the tip 26' is the thinnest portion of the outer needle 20'. The tissue slicing feature 90 may be, for example, a Franseen tip (as described above with reference to FIGS. 4-5 and as shown in FIG. 6-7). Other suitable slicing configurations may be a Trocar tip, a Quinke tip or any other needle point feature that forms a sharp tip and edge.

In this embodiment, the thickness 76 of the outer needle 20' varies along its length due to the introduction of the described features. The thickness 76 of the outer needle 20' between the hub 22 and the inner end 82 of the forcing cone 80 may be approximately 0.003 or 0.004 inches. The thickness 76 of the outer needle 20' begins to decrease by the angle γ at the inner end 82 of the forcing cone 80 and begins to decrease further by the angle α at the valleys 94 of the tissue slicing feature 90. The thickness 76 at the tip 26' may be thus reduced to approximately 0.0012 to 0.0014 inches.

The result of the embodiment described above, including both the countersink or forcing cone 80 and the tissue slicing feature 90, is a complete and uniform core sample trapped within the end of the outer needle 20', without any crush artifact. The tissue slicing feature 90 of the device 20' provides a cleaner cut with only linear motion and without rotation of the outer needle 20'. Furthermore, the countersink or forcing cone 80 of the device 20' provides a guiding surface to guide and support the core as it is cut away from the tissue by the cutting edge 78 of the outer needle 20'.

The outer needle 20' may include other tissue retention features formed in the inner surface 72 of the outer needle in conjunction with or in lieu of the forcing cone 80. Thus, in one feature a spiral groove 85 is formed in the inner surface 72. The groove 85 may be formed in the inner surface 72 at a location adjacent the inner end 82 of the forcing cone 80, as shown in FIG. 7. In this embodiment, the groove 85 has a depth of 0.04 to 0.08 inches. The groove 85 is shown as commencing at the end 82 of the forcing cone, although in other embodiments the groove may overlap the forcing cone. It is believed that the groove enhances the "grip" between the outer needle and the tissue being excised, particularly when combined with the forcing cone 80. It is contemplated that other tissue retention features may be incorporated into the inner surface 72 of the outer cannula. For instance, rather than a spiral groove, such as the groove 85, the feature may include a series of circumferential grooves, axial grooves, striations, ridges, knurling or other features that provide an irregular surface into which the tissue may swell. However, the spiral groove may be preferred for manufacturing reasons.

In one embodiment, the outer needle 20 of the full core biopsy device 10 may include a countersink or forcing cone 80 along with a predetermined relative positioning between the inner needle 30 and the outer needle 20'. In this embodiment, the inner needle 30 can have a length that maintains the inner needle tip 36 in a position (not shown) such that the inner needle tip 36 is situated in the outer needle 20' between the hub 22 and the inner end 82 of the countersink or forcing cone 80. In other words, the tip of the inner needle may be offset proximal or inboard of the inner end 82 of the forcing cone 80. This embodiment combines the advantages provided by the relative positioning of the inner and outer needles (in the same manner as described above in reference to the inner needle 30 and outer needle 20 of FIGS. 4-5) with the advantages provided by the forcing cone 80 as described above. Likewise, the other retention features, such as the spiral groove 85, may be incorporated into the full core biopsy device 20.

The inner needle tip 36 may be closed or blocked to prevent tissue ingress into the inner needle 30. In another approach, the inner needle 30 may be integrated into an irrigation or aspiration/vacuum system. In this approach the inner needle 30 is hollow with the proximal end coupled to an irrigation or aspiration component. In order to ensure that tissue does not enter the inner needle 30, the tip 36 may be provided with a filter element that is configured to allow passage of fluids but not tissue.

Figure 8:
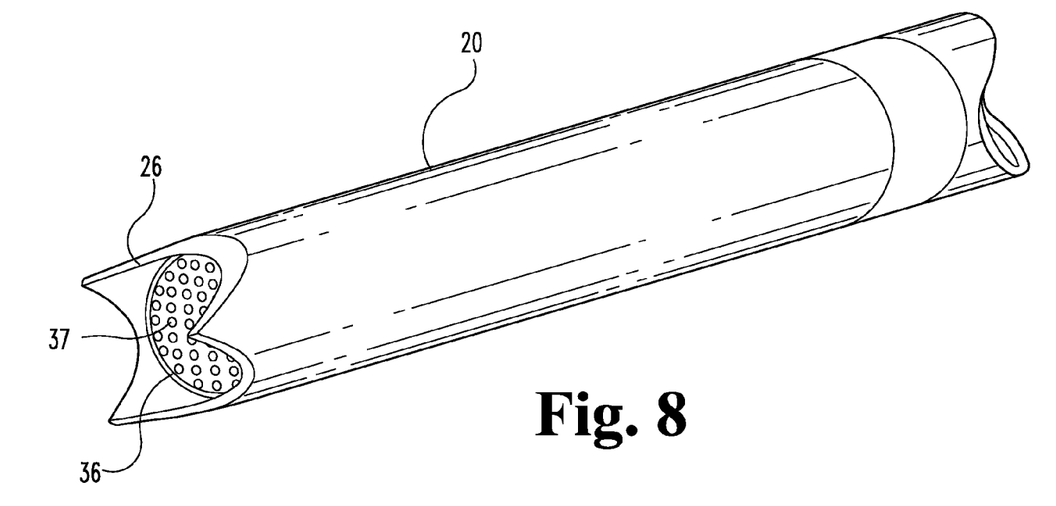
FIG. 8 is an enlarged end perspective view of an outer needle and an inner needle with a filter element for use with some embodiments of the full core biopsy core device of FIG. 1.

In one embodiment, the filter element is an etched membrane filter, such as the filter 37 shown in FIG. 8. The filter 37 may be made of 304 stainless steel and welded to the inner diameter of the hollow inner needle 30 at or adjacent the tip 36 of the needle 30. In one specific embodiment the membrane is about 0.002 inches thick with a series of 0.0037 inches diameter perforations distributed at a 0.0055 inches pitch around the area of the filter 37. Other filter element configurations are contemplated, such as a wire mesh construction.

The filter element may enhance the procedure for using the biopsy device 10 described above. For instance, in some procedures it may be desirable to apply suction at the outer needle tip 26 to help draw tissue into the outer needle 20 or to hold the tissue within the outer needle 20 as the biopsy device 10 is withdrawn from the patient. The inner needle 30 may thus be coupled to a device that provides suction at the inner needle tip 36. The filter element 37 can prevent ingress of tissue into the inner needle 30. A full core or other biopsy device can benefit from the incorporation of the filter element 37 particularly in combination with one or more of the tissue slicing feature 90, the tissue retention feature spiral groove 85, the forcing cone 80 and the relative positioning of the inner needle 30 and the outer needle 20, 20'.

With respect to the application of suction to assist in extracting the tissue sample, it is contemplated that only a short vacuum "burst" is needed to sufficiently retain the tissue sample within the outer needle 20, 20'. Thus, while the inner needle 30 may be connected to an external vacuum source, such an approach may not be practical or necessary for many applications of the full core biopsy device 10 disclosed herein. Consequently, a biopsy device 60 shown in FIG. 9 may be modified to incorporate a vacuum generation feature. The device 60 may be similar to the device 10 described above, with substantially the same housing 12, outer needle 20 and full core tip 26, and substantially the same hub 32 supporting the inner needle 30.

Figure 9:
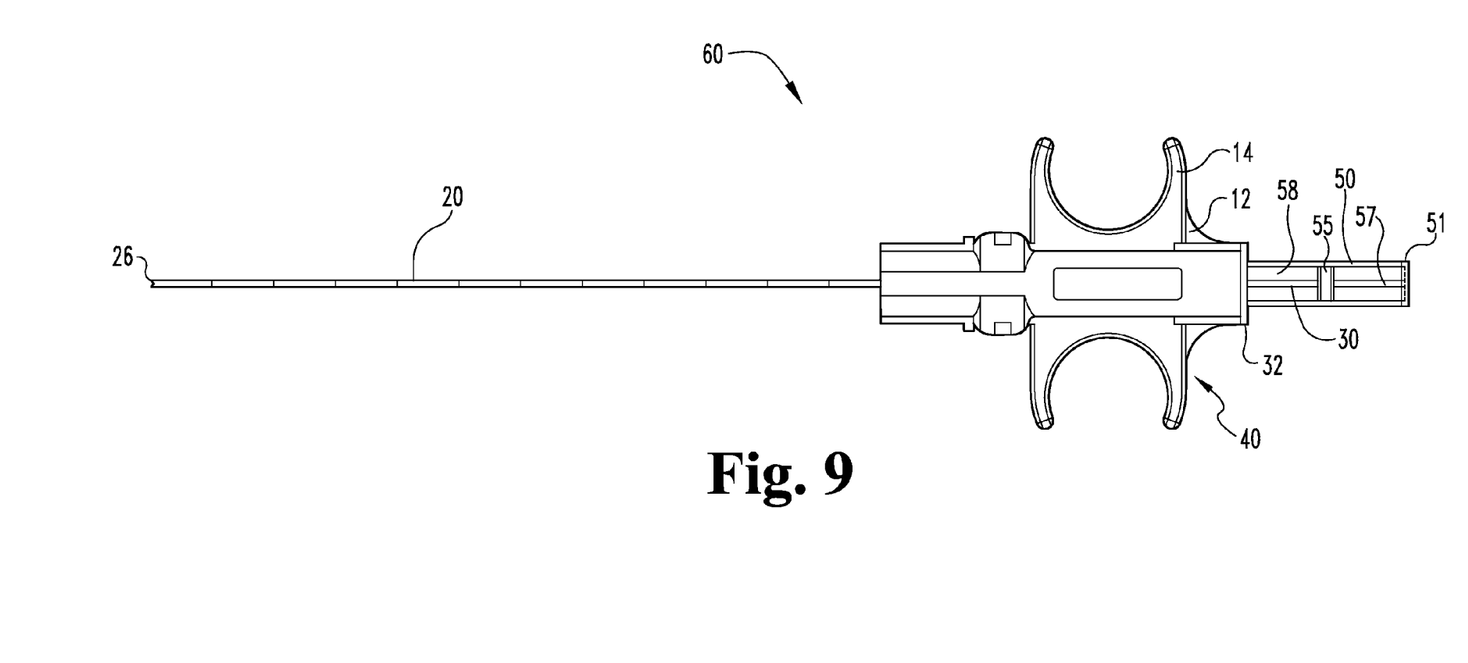
FIG. 9 is a perspective view of a full core biopsy device with a vacuum element according to one aspect of the present disclosure.

In this embodiment, the biopsy device 60 is modified to incorporate a vacuum element 50 mounted in sealed engagement with the inner needle hub 32. The inner needle 30 has a length sufficient to extend from the outer needle tip 26 to (or slightly beyond) the open end 51 of the vacuum element 50. A piston 55 is mounted on the proximal end of the inner needle 30 and slidably disposed within the vacuum chamber 58. The proximal end of the inner needle 30 may be provided with a handle 57 that can be used to pull the inner needle 30 back from the tip 26 of the outer needle 20, 20'. When the handle 57 is pulled back, the piston 55 draws a vacuum within the chamber 58, which in turn pulls a vacuum within the inner needle 30. The vacuum may be enhanced if the excised tissue impinges on the distal tip 36 of the inner needle 30. The inner needle 30 may be provided with openings that communicate between the lumen of the inner needle and the vacuum chamber 58.

In some embodiments the operation of the vacuum element 50 may be coordinated and automatic with the firing of the biopsy device 60. If the vacuum element 50 is operated too soon before the tissue sample has been captured by the outer needle 20, 20' little or no vacuum will be drawn within the inner needle 30. The vacuum may thus commence when the outer needle 20, 20' approaches the end of its cutting stroke to help draw the tissue into the outer needle 20, 20'. The vacuum is preferably maintained until the outer needle 20, 20' has begun to be withdrawn from the biopsy site. In prior full core biopsy devices, when the device is being withdrawn with excised tissue, resistance in the tissue sample may tend to pull the sample back to the biopsy site and out of the biopsy device. Providing suction as the biopsy device 60 is withdrawn can resist dislodgement or retraction of the tissue sample and ensure that the sample is completely separated from the original tissue site. However, it may be preferable that the vacuum be maintained for a limited duration to avoid sucking the tissue sample into the inner needle 30 (particularly if no filter 37 is present) which may compromise the integrity of the tissue sample for subsequent histopathology. Thus, the suction may be preferably applied for a duration less than the time to fully extract the biopsy device from the tissue site.

The amount of vacuum that can be drawn by the vacuum element 50 may be limited by limiting the stroke of the piston 55 mounted to the inner needle 30. It is contemplated that only minimal suction may be needed to ensure complete removal of the tissue sample upon withdrawal of the biopsy device 60. It is important that integrity of the tissue sample be preserved and unaffected by the suction.

In a further embodiment, the vacuum element 50 may be configured to pull the vacuum within the outer needle 20, 20'. In this case, the chamber 58 is in communication with the outer needle 20, 20', while the piston 55 remains mounted on the inner needle 30. In either embodiment, the suction is self-generated within the biopsy device 60 so no external vacuum source is necessary. This self-generation aspect insures that the amount of suction generated cannot exceed an acceptable value that might otherwise cause damage to the tissue or compromise the function of the device. Moreover, the vacuum may be generated consistently with each firing of the biopsy device 60 without the need to "reset" any components.

In some biopsy settings, it is desirable to obtain multiple tissue samples. In this case, after each firing of the biopsy device 60 the tissue sample may be dislodged by charging the outer needle 20, 20', but the position of the inner needle 30 may be unchanged (except in some cases in which the inner needle 30 is advanced slightly to assist in dislodging the tissue sample). The inner needle 30 may be biased to a starting position, not only for obtaining the sample but for generating the optimum vacuum when a sample is taken.

The foregoing detailed description of one or more embodiments of the biopsy device with an inner needle disposed within an outer needle has been presented herein by way of example and not limitation. It will be recognized that there are advantages to certain individual features and functions described herein. Moreover, it will be recognized that various alternatives, modifications, variations or improvements of the above-disclosed embodiments and other features and functions, or alternatives thereof, may be desirably combined into many other different embodiments, systems or applications. Presently unforeseen or unanticipated alternatives, modifications, variations or improvements therein may be subsequently made by those skilled in the art which are also intended to be encompassed by the appended claims.

What is claimed is:

1. A biopsy device comprising:
an outer needle hub;
an outer needle coupled at a proximal end to the outer needle hub, the outer needle including:
an outer needle tip at an opposite distal end;
a tissue slicing feature defined at said tip configured for slicing tissue; and
an inner surface including a countersink formed at said tip and tapered from a distalmost end of the outer needle;
an inner needle hub; and
an inner needle coupled at a proximal end to said inner needle hub, the inner needle including an inner needle tip at an opposite distal end, said inner needle coaxially disposed within said outer needle, wherein;
said tissue slicing feature includes a plurality of prongs and valleys between said prongs, said prongs and valleys defining a cutting edge for slicing tissue, said valleys defining a diameter; and
said countersink is tapered from said outer needle tip to an inner end located at a distance from said outer needle tip equal to twice said diameter.

2. The biopsy device of claim 1, wherein said countersink is tapered at approximately a three to four degree angle relative to the inner surface.

3. The biopsy device of claim 1, wherein said tissue slicing feature is a Franseen tip.

4. The biopsy device of claim 1, wherein said outer needle includes a tissue retention feature defined in said inner surface between said tissue slicing feature and said proximal end of said outer needle.

5. The biopsy device of claim 4, wherein said tissue retention feature includes a groove defined in said inner surface.

6. The biopsy device of claim 5, wherein said groove is a spiral groove.

7. The biopsy device of claim 1, further comprising:
a mechanism coupled to said outer needle hub and said inner needle hub for charging and firing said outer needle relative to said inner needle to capture a tissue sample within said outer needle tip,
wherein said inner needle and said outer needle are sized so that said inner needle tip is always proximal of the distalmost end of said outer needle when the outer needle is charged and fired.

8. The biopsy device of claim 1, further comprising:
a vacuum generating component including;
a chamber in communication with said proximal end of said inner needle;
a piston coupled to said proximal end of said inner needle and slidably disposed within said chamber; and
a handle coupled to said proximal end of said inner needle configured to manually pull the inner needle and said piston therewith to draw a vacuum within said chamber.

9. The biopsy device of claim 8, wherein said inner needle includes a filter covering said inner needle tip.

10. The biopsy device of claim 9, wherein said filter is an etched membrane filter.

11. The biopsy device of claim 8, wherein said chamber is in communication with the proximal end of said outer needle.

12. The biopsy device of claim 1, wherein said inner needle is hollow and includes a filter covering said inner needle tip.

13. The biopsy device of claim 12, wherein said filter is an etched membrane filter.

* * * * *